United States Patent [19]

LaPierre et al.

[11] Patent Number: 4,855,530
[45] Date of Patent: Aug. 8, 1989

[54] ISOMERIZATION PROCESS

[75] Inventors: Rene B. LaPierre, Medford; Randall D. Partridge, Princeton, both of N.J.; Steven S. Wong, Langhorne, Pa.

[73] Assignee: Mobil Oil Corporation, New York, N.Y.

[21] Appl. No.: 183,399

[22] Filed: Apr. 13, 1988

Related U.S. Application Data

[63] Continuation of Ser. No. 81,533, Aug. 4, 1987, abandoned, which is a continuation of Ser. No. 379,423, May 18, 1982, abandoned.

[51] Int. Cl.$^4$ ................................................ C07C 5/13
[52] U.S. Cl. ..................................... 585/739; 208/138
[58] Field of Search .......................... 585/739; 208/138

[56] References Cited

U.S. PATENT DOCUMENTS

| | | | |
|---|---|---|---|
| 3,190,939 | 6/1965 | Benesi | 585/739 |
| 3,354,078 | 11/1967 | Miale et al. | 585/739 |
| 3,392,108 | 7/1968 | Mason | 208/111 |
| 3,442,795 | 5/1969 | Kerr | 208/120 |
| 3,507,931 | 4/1970 | Morris et al. | 585/739 |
| 3,673,267 | 6/1972 | Chen et al. | 585/739 |
| 3,714,029 | 1/1973 | Berry | 585/739 |
| 3,751,502 | 8/1973 | Hayes et al. | 585/739 |
| 3,861,005 | 1/1975 | Steinmetz | 208/111 |
| 4,146,462 | 3/1979 | Rustamov et al. | 585/739 |
| 4,232,181 | 11/1980 | Kiovsky et al. | 585/739 |
| 4,238,319 | 12/1980 | Hauschildt et al. | 208/138 |
| 4,357,233 | 11/1982 | Dwyer et al. | 585/739 |
| 4,401,556 | 8/1983 | Bezman et al. | 208/111 |
| 4,419,220 | 12/1983 | LaPierre et al. | 208/111 |
| 4,501,926 | 2/1985 | LaPierre et al. | 585/739 |
| 4,518,485 | 5/1985 | LaPierre et al. | 208/89 |
| 4,541,919 | 9/1985 | LaPierre et al. | 208/111 |

FOREIGN PATENT DOCUMENTS

| | | |
|---|---|---|
| 28938 | 12/1980 | European Pat. Off. . |
| 121924 | 9/1976 | Fed. Rep. of Germany . |
| 2041397 | 9/1980 | United Kingdom . |

OTHER PUBLICATIONS

"Shape-Selectivity Changes in High-Silica Zeolites", Jacobs et al., Faraday Disc. Chem. Soc. (1982), 72, 353, p. 361.

"The Influence of Chain Length in Hydrocracking and Hydroisomerization of n-Alkanes", Weitkamp, ACS Symp. Ser., p. 1 (1975).

"Ultrastable Zeolites as Catalysts for Hydrocracking n-Decane", Steijns et al., Erdol und Kohle-Erdgat, bd31, Heft12, Dec. 78, p. 581.

Primary Examiner—Curtis R. Davis
Attorney, Agent, or Firm—Alexander J. McKillop; Charles J. Speciale; Marina V. Schneller

[57] ABSTRACT

Long chain ($C_{7+}$) paraffins are isomerized over a large pore, highly siliceous zeolite catalyst such as zeolite Y or ZSM-20 having a structural silica:alumina ratio of at least 10:1. The use of the highly siliceous zeolite inhibits the degree of cracking and also permits weaker hydrogenation components such as palladium to be used in the catalyst.

33 Claims, 7 Drawing Sheets

FIG. 5
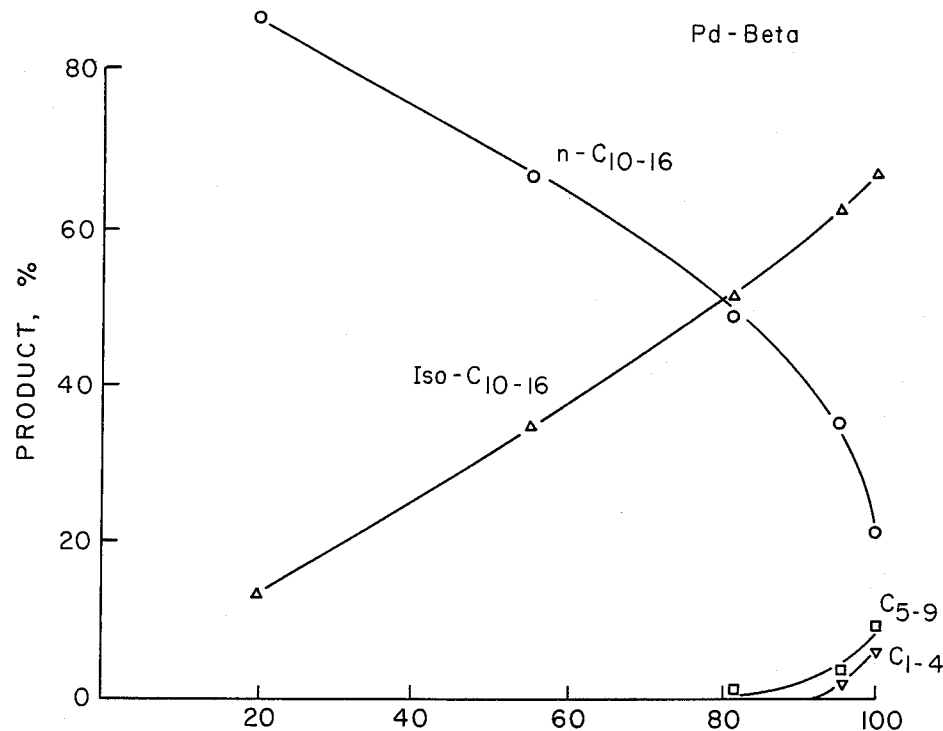
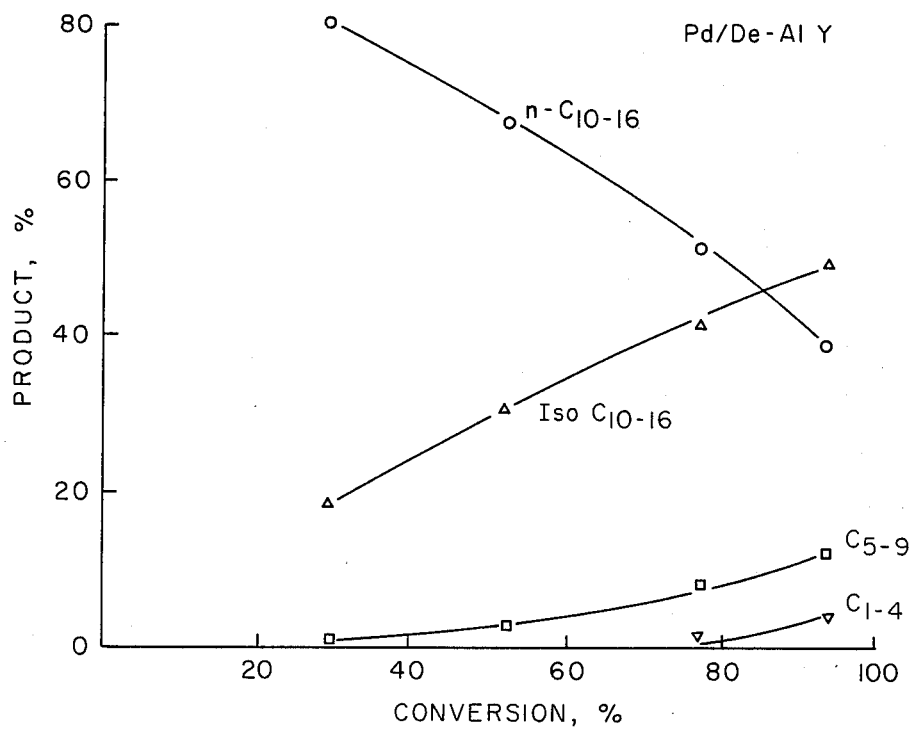

ISOMERIZATION PROCESS

This is a continuation of copending application Ser. No. 081,533, filed on Aug. 4, 1987, and now abandoned, which is a continuation of application Ser. No. 379,423, filed on May 18, 1982, and now abandoned.

FIELD OF THE INVENTION

This invention relates to isomerization and, more particularly, to a process for isomerizing paraffins.

THE PRIOR ART

A unit process which is frequently encountered in petroleum refining is isomerization. In this process, as conventionally operated, low molecular weight $C_4$ and $C_6$ n-paraffins are converted to iso-paraffins in the presence of an acidic catalyst such as aluminum chloride or an acidic zeolite as described in G.B. No. 1,210,335. Isomerization processes for pentane and hexane which operate in the presence of hydrogen have also been proposed but since these processes operate at relatively high temperatures and pressures, the isomerization is accompanied by extensive cracking induced by the acidic catalyst, so that a substantial proportion of useful products is degraded to products of lower value.

Isomerization processes have, in general, been confined to applications with lower molecular weight alkanes such as butane, pentane and hexane, as mentioned above, but some investigations have been made into the isomerization of longer chain alkanes over various types of catalyst. A fluorinated platinum on alumina catalyst is described in Ind. Eng. Chem. Prod. Res. Devel. 8, 154 (1969) and the use of platinum and palladium on zeolite Y for the hydroisomerization of longer chain ($C_{10}$–$C_{16}$) n-alkanes is described in ACS Symposium Series, Vol. 20, (Weitkamp, J.) A.C.S., Washington, D.C., 1975. The catalysts used in the processes are materials with a relatively high degree of acidic functionality which, in the case of the zeolites at least, is conferred by reason of their relatively high alumina content, the zeolite having a silica:alumina ration of about 5:1. Although a certain amount of acidic functionality is essential to the mechanism of isomerization, it also tends to induce cracking reactions which, as mentioned above, tend to degrade the feedstock to products of lower value. To a certain extent, the presence of an excess of acidic functionality can be offset by the use of a strong hydrogenation component such as platinum, but even then, the known types of catalyst all tend to promote an excessive degree of cracking during the isomerization process.

SUMMARY OF THE INVENTION

It has now been found that the selectivity of the catalyst to isomerization may be increased by the use of a highly siliceous large pore zeolite such as zeolite Y, zeolite beta or zeolite ZSM-20. The highly siliceous nature of the zeolites reduces their acidic functionality so that cracking is minimized and isomerization favored. This reduction in acidic functionality makes it possible to use hydrogenation components in the catalyst which are less active because the acidic nature of the catalyst does not need to be balanced to such a great degree by a strong hydrogenation catalyst; palladium and other metals such as nickel may also be used as the hydrogenation component.

The isomerization process is operated with a hydrocarbon feedstock which contains long chain ($C_{7+}$) n-paraffins. During the isomerization these waxy paraffinic components are isomerized to iso-paraffins which are inherently less waxy. The isomerized product therefore has a lower pour point and may be used in applications where low temperature performance is required, e.g., in jet fuels, diesel fuels, lubricating oils and heating oils. The extent of cracking is, however, reduced so that the total liquid yield of the process is improved. A further advantage of the present process is that the present catalysts show less deactivation than catalysts prepared from less siliceous zeolites; this advantage is maintained even with the weaker hydrogenation components such as palladium.

Because the present process offers the possibility of reducing the content of waxy, n-paraffins it may be used for dewaxing purposes. In addition, however, the iso-paraffins which are produced by the isomerization usually have higher octane ratings that the straight chain paraffins from which they are derived. The present process therefore offers the possibility of producing high octane naphthas and gasolines as well as low pour point jet fuels, diesel fuels, heating oils and lubricating oils from highly paraffinic feedstocks.

BRIEF DESCRIPTION OF THE DRAWINGS

FIGS. 1 to 7 of the accompanying drawings are graphical presentations of the results of isomerization studies reported in Examples 11 to 15 below.

DESCRIPTION OF PREFERRED EMBODIMENTS

Feedstock

Figure 1:
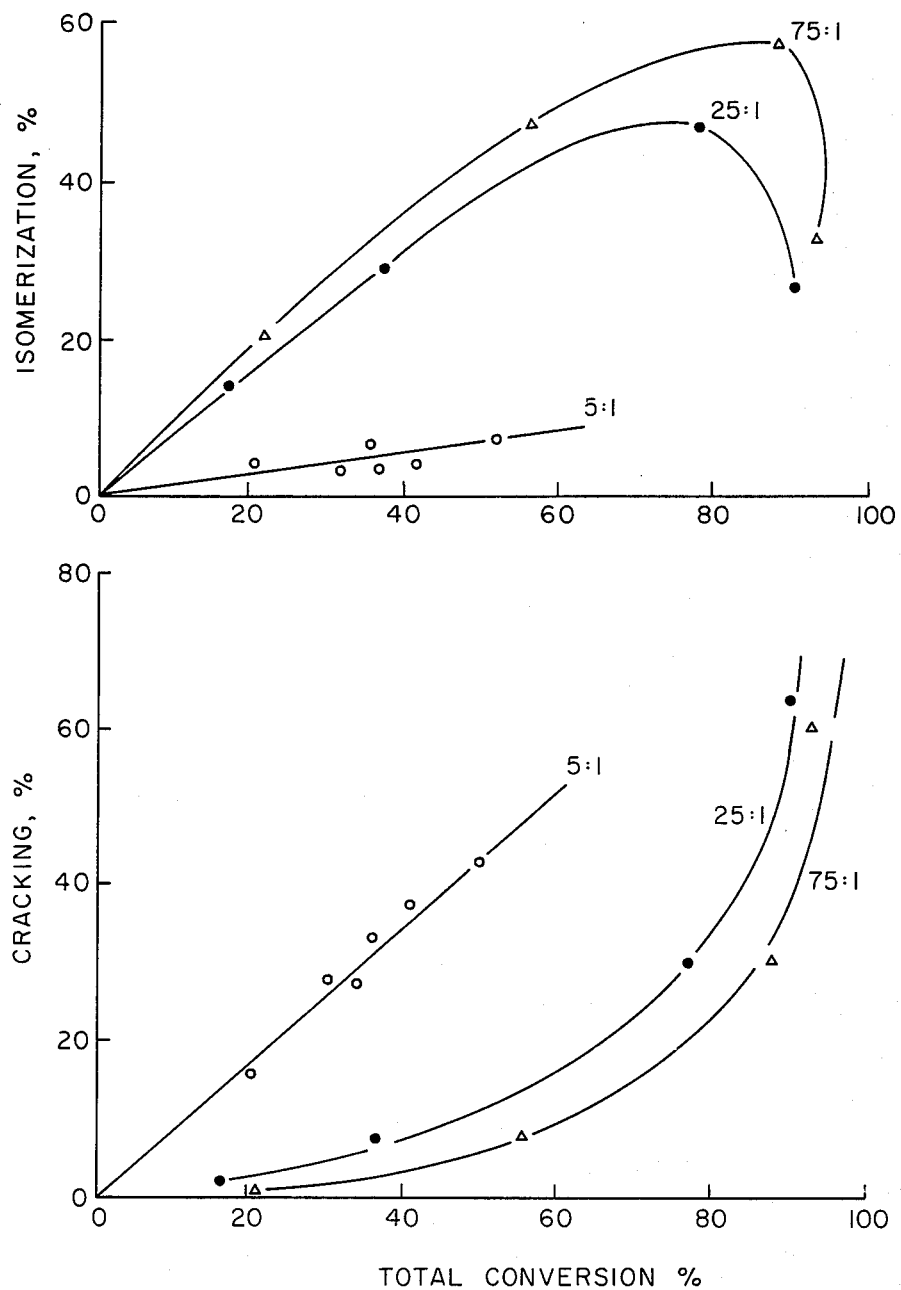

The feedstock for the process is one which contains significant amounts of longer chain ($C_{7+}$) n-alkanes, especially n-paraffins in the range $C_{10}$ to $C_{40}$. Generally, the feedstock will be a $C_{10+}$ feed since feedstocks of this type benefit most by removal of the waxy straight chain paraffins when a dewaxed, low pour point product is desired. Feedstocks of this kind will normally have an initial boiling point of 150° C. (about 300° F.) and may be selected from a wide range of petroleum refinery streams from distillates to residual products, including kerosenes, gas oils (light and heavy), reduced crudes (atmospheric and vacuum), deasphalted residua, catalytic cracking tower bottoms, coker tower bottoms, hydrocracker effluents and crudes. Oils derived from shales, tar sands and coal may also be heated in this way. The feedstock will typically have a boiling range of about 260° C. to 560° C. (500° F. to 1050° F.) and more usually about 340° C. to 540° C. (about 650° F. to 1000° F.). Lubricating oil stocks will normally have a boiling range of 340° C. to 540° C.

During the isomerization process the n-paraffins in the feedstock will be converted to iso-paraffins. Generally, the presence of aromatics is undesirable although single ring aromatics which are readily hydrogenated over the metal component of the catalyst can be tolerated; polycyclic aromatics which are commonly found in the higher boiling fractions (IBP over 340° C.) are undesirable because they are preferentially sorbed on most of the present class of catalysts, thereby precluding the paraffins from access to the catalytic sites and so inhibiting the desired isomerization. The aromatic content may, for preference, be held below 10 weight percent although slightly greater amounts up to about 20 weight percent might be tolerated if the proportion of monocyclic aromatics is sufficiently high and if a sufficiently strong hydrogenation component such as platinum is present on the catalyst.

Catalyst

The catalyst used in the process is a large pore crystalline zeolite. Many crystalline zeolites are known. Some occur (at least so far) only in nature, for instance paulingite and merlinoite: some occur only as a result of synthesis, for instance zeolites A and ZSM-5: and some occur in both natural and synthetic forms, for instance mordenite, a synthetic counterpart of which is known as Zeolon, and faujasite, synthetic counterparts of which are known as zeolites X and Y. Counterparts are of course demonstrated as such by correspondence of their X-ray diffraction data, the indicia by means of which the individuality of a zeolite is established. Such data are a manifestation of the particular geometry of the three-dimensional lattice, formed of $SiO_4$ and $AlO_4$ tetrahedra crosslinked by the sharing of oxygen atoms and including sufficient cationic complement to balance the resulting negative charge on the $AlO_4$ tetrahedra, of which a zeolite consists.

The chemical formula of a zeolite is thus $$M_{x/n}:(AlO_2)_x:(SiO_2)_y$$

where M is a cation of valence n and x and y are the number of aluminum and silicon atoms, respectively, in the unit cell. This expression is however frequently transformed into the mole ratio of oxides form.

$$M_{2/n}O:Al_2O_3:y/2x SiO_2/$$

which is of course empirically ascertainable and thus the only formula which can be ascribed to a zeolite when its unit cell contents are unknown. Since the only significant quantity in such a formula is the term y/2x, and since this term (which is almost invariably a range) can usually be satisfied by many zeolites of widely differing lattice geometry, chemical formula is not of value in establishing the identity of a zeolite. Furthermore, such a formula frequently expresses artefact when empirically derived, the cationic-valence-/aluminum-atoms ratio deviating from the unity which it must in fact be: and it fails to provide for zeolites whose lattice structure can be brought into existence from reaction mixtures from which alumina is excluded.

The zeolites which are used in the present process are characterized by a porous lattic structure which possesses pores having a minimum dimension of at least 6 Angstroms. In addition, the zeolite is to have a structural silica:alumina ratio of 10:1 or more, preferably much higher e.g. 20:1, 50:1, 100:1, 200:1 or 500:1. Zeolites of this type may also be characterized in terms of their Constraint Index and their hydrocarbon sorption capacity.

Zeolites have a crystal structure which is capable of regulating the access to an egress from the intracrystalline free space. This control, which is effected by the crystal structure itself, is dependent both upon the molecular configuration of the material which is or, alternatively, is not, to have access to the internal structure of the zeolite and also upon the structure of the zeolite itself. The pores of the zeolite are in the form of rings which are formed by the regular disposition of the tetrahedra making up the anionic framework of the crystalline aluminosilicate, the oxygen atoms themselves being bonded to the silicon or aluminum atoms at the centers of the tetrahedra. A convenient measure of the extent to which a zeolite provides this control for molecules of varying sizes to its internal structure is provided by the Constraint Index of the zeolite: zeolites which provide but highly restricted access to and egress from the internal structure have a high value for the Constraint Index and zeolites of this kind usually have pores of small size. Contrariwise, zeolites which provide relatively free access to the internal zeolite structure have a low value for the Constraint Index. The method by which Constraint Index is determined is described fully in U.S. Pat. No. 4,016,218 to which reference is made for details of the method together with examples of Constraint Index for some typical zeolites. Because Constraint Index is related to the crystalline structure of the zeolite but is nevertheless determined by means of a test which exploits the capacity of teh zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, be varied by artifices including base exchange, steaming or control of silica:alumina ratio.

Consistent with the minimum pore size limitation mentioned above the zeolites used in the present process should have a Constraint Index in the range of up to 2.0 and usually, the Constraint Index will fall in the range 0.5 to 2.9. Because the isomerization selectivity becomes lower with smaller pore size in the zeolite, the larger pore materials which conform to these limitations will be preferred. Zeolites which may be used in the present process include zeolite Y, zeolite beta, mordenite and zeolites ZSM-12, ZSM-20 and ZSM-50. Zeolite ZSM-12 is described in U.S. Pat. No. 3,832,449, ZSM-20 in U.S. Pat. No. 3,972,983 and ZSM-50 in U.S. patent application Ser. No. 343,631 of E. W. Valyocsik, filed Jan. 28, 1982, and entitled "Zeolite ZSM-50, Method of Preparing Same and Catalytic Conversion Therewith". Highly siliceous forms of ZSM-12 are described in U.S. patent applications Ser. Nos. 3,144 and 3,146 filed Jan. 15, 1979. Reference is made to these patents and applications for details of these zeolites and their preparation.

Another property which characterizes the zeolites which may be used in the present catalysts is their hydrocarbon sorption capacity. The zeolite used in the present catalysts should have a hydrocarbon sorption capacity for n-hexane of greater than 5 preferably greater than 6 percent by weight at 50° C. The hydrocarbon sorption capacity is determined by measuring the sorption at 50° C., 20 mm Hg (2666 Pa) hydrocarbon pressure in an inert carrier such as helium.

Hydrocarbon sorption capacity (%) =

$$\frac{\text{Wt. of hydrocarbon sorbed}}{\text{Wt. of zeolite}} \times 100$$

The sorption test is conveniently carried out in a TGA with helium as a carrier gas flowing over the zeolite at 50° C. The hydrocarbon of interest e.g. n-hexane is introduced into the gas stream adjusted to 20 mm Hg hydrocarbon pressure and the hydrocarbon uptake, measured as the increase in zeolite weight is recorded. The sorption capacity may then be calculated as a percentage.

If the zeolite selected may be produced in the desired highly siliceous form by direct synthesis, this will often be the most convenient method for obtaining it. Zeolite beta, for example, is known to be capable of being synthesized directly in forms having silica:alumina ratios up to 100:1, as described in U.S. Pat. Nos. 3,308,069 and Re. 28,341 which describe zeolite beta, its preparation and properties in detail. Reference is made to these patents for these details. Zeolite Y, on the other hand, can be synthesized only in forms which have silica:alumina ratios up to about 5:1 and in order to achieve higher ratios, resort may be made to varius techniques to remove structural aluminum so as to obtain a more highly siliceous zeolite. The same is true of mordenite which, in its natural or directly synthesized form has a silica:alumina ratio of about 10:1. Zeolite ZSM-20 may be directly synthesized with silica:alumina ratios of 7:1 or higher, typically in the range of 7:1 to 10:1, as described in U.S. Pat. Nos. 3,972,983 and 4,021,331 to which reference is made for details of this zeolite, its preparation and properties. Zeolite ZSM-20 also may be treated by various methods to increase its silica:alumina ratio.

Control of the silica:alumina ratio of the zeolite in its as-synthesized form may be exercised by an appropriate selection of the reltive proportions of the starting materials, especially the silica and alumina precursors, a relatively smaller quantity of the alumina precursor resulting in a higher silica:alumina ratio in the product zeolite, up to the limit of the synthetic procedure. If higher ratios are desired and alternative syntheses affording the desired high silica:alumina ratios are not available, other techniques such as those described below may be used in order to prepare the desired highly siliceous zeolites.

It should be understood that the silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite sructure are employed. Due care should therefore be taken to ensure that the framework silica:alumina ratio is correctly determined.

A number of different methods are known for increasing the structural silica:alumina ratio of various zeolites. Many of these methods rely upon the removal of aluminum from the structural framework of the zeolite by chemical agents appropriate to this end. A considerable amount of work on the preparation of aluminum deficient faujasites has been performed and is reviewed in Advances in Chemistry Series No. 121, Molecular Sieves, G. T. Kerr, American Chemical Society, 1973. Specific methods for preparing dealuminized zeolites are described in the following, and reference is made to them for details of the method: Catalysis by Zeolites (International Symposium on Zeolites, Lyon, Sept. 9–11, 1980), Elsevier Scientific Publishing Co., Amsterdam, 1980 (dealuminization of zeolite Y with silicon tetrachloride); U.S. Pat. No. 3,442,795 and G.B. No. 1,058,188 (hydrolysis and removal of aluminum by chelation); G.B. No. 1,061,847 (acid extraction of aluminum); U.S. Pat. No. 3,493,519 (aluminum removal by steaming and chelation); U.S. Pat. No. 3,591,488 (aluminum removal by steaming); U.S. Pat. No. 4,273,753 (dealuminization by silicon halides and oxyhalides); U.S. Pat. No. 3,691,099 (aluminum extraction with acid); U.S. Pat. No. 4,093,560 (dealuminization by treatment with salts); U.S. Pat. No. 3,937,791 (aluminum removal with Cr(III) solutions); U.S. Pat. No. 3,506,400 (steaming followed by chelation); U.S. Pat. No. 3,640,681 (extraction of aluminum with acetylacetonate followed by dehydroxylation); U.S. Pat. No. 3,836,561 (removal of aluminum with acid); DE-OS No. 2,510,740 (treatment of zeolite with chlorine or chlorine-contrary gases at high temperatures), NL No. 7,604,264 (acid extraction), JA No. 53,101,003 (treatment with EDTA or other materials to remove aluminum) and J. Catalysis 54 295 (1978) (hydrothermal treatment followed by acid extraction).

Because of their convenience and practicality the preferred dealuminization methods for preparing the present highly siliceous zeolites are those which rely upon acid extraction of the aluminum from the zeolite. It has been found that zeolite beta may be readily dealuminized by acid extraction and details of a suitable method are given in U.S. patent application Ser. No. 379,399, filed May 18, 1982, and now abandoned, by R.B. LaPierre and S.S. Wone, entitled "High Silica Zeolite Beta", and reference is made to this application for details of the method.

Briefly, the method comprises contacting the zeolite with an acid, preferably a mineral acid such as hydrochloric acid. The dealuminization proceeds readily at ambient and mildly elevated temperatures and occurs with minimal losses in crystallinity, to form high silica forms of zeolite beta with silica:alumina ratios of at least 100:1, with ratios of 200:1 or even higher being readily attainable.

The zeolite is conveniently used in the hydrogen form for the dealuminization process although other cationic forms may also be employed, for example, the sodium form. If these other forms are used, sufficient acid should be employed to allow for the replacement by protons of the original cations in the zeolite. The amount of zeolite in the zeolite/acid mixture should generally be from 5 to 60 percent by weight.

The acid may be a mineral acid i.e., an inorganic acid or an organic acid. Typical inorganic acids which can be employed include mineral acids such as hydrochloric, sulfuric, nitric and phosphoric acids, peroxydisulfonic acid, dithionic acid, sulfamic acid, peroxymonosulfuric acid, amidosulfonic acid, nitrosulfonic acid, chlorosulfuric acid, pyrosulfuric acid, and nitrous acid. Representative organic acids which may be used include formic acid, trichloroacetic acid, and trifluoroacetic acid.

The concentration of added acid should be such as not to lower the pH of the reaction mixture at an undesirably low level which could affect the crystallinity of the zeolite undergoing treatment. The acidity which the zeolite can tolerate will depend, at least in part, upon the silica:alumina ratio of the starting material. Generally, it has been found that zeolite beta can withstand concentrated acid without undue loss in crystallinity but as a general guide, the acid will be from 0.1 N to 4.0 N, usually 1 to 2 N. These values hold good regardless of the silica:alumina ratio fo the zeolite beta starting material. Stronger acids tend to effect a relatively greater degree of aluminum removal than weaker acids.

Higher silica:alumina ratios in the product may be obtained with starting materials of relatively lower silica:alumina ratio e.g., below 30:1.

The dealuminization reaction proceeds readily at ambient temperatures but mildly elevated temperatures may be employed e.g. up to 100° C. The duration of the extraction will affect the silica:alumina ratio of the product since extraction, being diffusion controlled, is time dependent. However, because the zeolite becomes progressively more resistant to loss of crystallinity as the silica:alumina ratio increases i.e. it becomes more stable as the aluminum is removed, higher temperatures and more concentrated acids may be used towards the end of the treatment than at the beginning without the attendant risk of losing crystallinity.

After the extraction treatment, the product is water washed free of impurities, preferably with distilled water, until the effluent wash water has a pH within the approximate range of 5 to 8.

Catalytic materials for particular uses can be prepared by replacing the cations as required with other metallic or ammoniacal ions. If calcination is carried out prior to ion exchange, some or all of the resulting hydrogen ions can be replaced by metal ions in the ion exchange process. The silica:alumina ratio will be at least 100:1 and preferably at least 150:1. Ratios of 200:1 or higher e.g. 250:1, 300:1, 400:1 or 500:1 may be obtained by use of this procedure. If desired, the zeolite may be steamed prior to acid extraction so as to increase the silica:alumina ratio and render the zeolite more stable to the acid. The steaming may also serve to increase the ease with which the aluminum is removed and to promote the retention of crystallinity during the extraction procedure.

Highly siliceous forms of zeolite Y may be prepared steaming or by acid extraction of structural aluminum (or both) but because zeolite Y in its normal, as-synthesized condition, is unstable to acid, it must first be converted to an acid-stable form. Methods for doing this are known and one of the most common forms of acid-resistant zeolite Y is known as "Ultrastable Y" (USY); it is described in U.S. Pat. Nos. 3,293,192 and 3,402,996 and the publication, Society of Chemical Engineering (London) Monograph Molecular Sieves, page 186 (1968) by C. V. McDaniel and P. K. Maher, and reference is made to these for details of the zeolite and its preparation. In general, "ultrastable" refers to Y-type zeolite which is highly resistant to degradation of crystallinity by high temperature and steam treatment and is characterized by a $R_2O$ content (wherein R is Na, K or any other akali metal ion) of less than 4 weight percent, preferably less than 1 weight percent, and a unit cell size less than 24.5 Angstroms and a silica to alumina mole ratio in the range of 3.5 to 7 or higher. The ultrastable form of Y-type zeolite is obtained primarily by a substantial reduction of the alkali metal ions and the unit cell size redution of the alkali metal ions and the unit cell size reduction. The ultrastable zeolite is identified both by the smaller unit cell and the low alkali metal content in the crystal structure.

The ultrastable form of the Y-type zeolite can be prepared by successively base exchanging a Y-type zeolite with an aqueous solution of an ammonium salt, such as ammonium nitrate, until the alkali metal content of the Y-type zeolite is reduced to less than 4 weight percent. The base exchanged zeolite is then calcined at a temperature of 540° C. to 800° C. for up to several hours, cooled and successively base exchanged with an aqueous solution of an ammonium salt until the alkali metal content is reduced to less than 1 weight percent, followed by washing and calcination again at a temperature of 540° C. to 800° C. to produce an ultrastable zeolite Y. The sequence of ion exchange and heat treatment results in the substantial reduction of the alkali metal content of the original zeolite and results in a unit cell shrinkage which is believed to lead to the ultra high stability of the resulting Y-type zeolite.

The ultrastable zeolite Y may then be extracted with acid to produce a highly siliceous form of the zeolite. The acid extraction may be made in the same way as described above for zeolite beta.

Other methods for increasing the silica:alumina ratio of zeolite Y by acid extraction are described in U.S. Pat. Nos. 4,218,307, 3,591,488 and 3,691,099, to which reference is made for details of these methods.

A preferred method for preparing highly siliceous forms of faujasite zeolites such as zeolite Y and ZSM-20 is described in U.S. patent application Ser. No. 379,424, filed May 18, 1982 and now abandoned by R. B. LaPierre and R. D. Partridge and P. T. Reischmann, entitled "Method for Preparing Acid Stable Zeolites and High Silica Zeolites Prepared by It" and reference is made to that application for detail of the method.

Zeolite ZSM-20 may be converted to more highly siliceous forms by a process similar to that used for zeolite Y: first, the zeolite is converted to an "ultrastable" form which is then dealuminized by acid extraction. The conversion to the ultrastable form may suitably be carried out by the same sequence of steps used for preparing ultrastable Y. The zeolite is successively base-exchanged to the ammonium form and calcined, normally at temperatures above 700° C. The calcination should be carried out in a deep bed in order to impede removal of gaseous products, as recommended in Advances in Chemistry Series, No. 121, op cit. Acid extraction of the "ultrastable" ZSM-20 may be effected in the same way as described above for zeolite beta.

Highly siliceous forms of mordenite may be made by acid extraction procedures of the kind described, for example, in U.S. Pat. Nos. 3,691,099, 3,591,488 and other dealuminization techniques which may be used for mordenite are disclosed, for example, in U.S. Pat. Nos. 4,273,753, 3,493,519 and 3,442,795. Reference is made to these patents for a full description of these processes.

The isomerization reaction is one which requires but a small degree of acidic functionality in the catalyst. Because of this, the zeolite may have a very high silica:alumina ratio since this ratio is inversely related to the acid site density of the catalyst. Thus, structural silica:alumina ratios of 100:1 or higher are preferred and in fact the ratio may be much higher e.g. 200:1, 500:1, 1000:1 or even higher. Since zeolites are known to retain their acidic functionality even at very high silica:alumina ratios of the order of 25,000:1, ratios of this magnitude or even higher are contemplated.

In addition to the zeolite component, the catalyst also contains a hydrogenation-dehydrogenation component which is preferably a noble metal of Group VIIIA of the Periodic Table (the Periodic Table referred to in this specification is the table approved by IUPAC and the U.S. National Bureau of Standards shown, for example, in the table of Fisher Scientific Company, Catalog No. 5-702-10). The preferred hydrogenation component is platinum but other noble metals such as palladium, gold, rhenium or rhodium may also be used. Combinations of noble metals such as platinum-rhenium, platinum-palladium, platinum-iridium or platinum-iridium-rhenium together with combinations with non-noble metals, particularly of Groups VIA and VIIIA are of interest, particularly with metals such as cobalt, nickel, vanadium, tungsten, titanium and molybdenum, for example, platinum-tungsten, platinum-nickel or platinum-nickel-tungsten. It is surprising that the highly siliceous zeolites permit relatively weak hydrogenation components such as palladium to be readily used because the more acidic zeolites such as zeolite Y (silica:alumina ratio about 5:1) have but poor selectivity for isomerization when combined with the weaker hydrogenation components such as palladium. In addition, the catalysts based on the highly siliceous zeolites in combination with the weaker hydrogenation components exhibit negligible deactivation even though similar catalysts prepared from low silica zeolites (silica:alumina ratio less than 10:1) become significantly deactivated in the course of use.

The metal may be incorporated into the catalyst by any suitable method such as impregnation or exchange onto the zeolite. The metal may be incorporated in the form of a cationic, anionic or neutral complex, such as $Pt(NH_3)_2^{+4}$, and cationic complexes of this type will be found convenient for exchanging metals onto the zeolite. Anionic complexes are also useful for impregnating metals into the zeolites.

The amount of the hydrogenation-dehydrogenation component is suitably from 0.01 to 10 percent by weight, normally 0.1 to 5 percent by weight, although this will, of course, vary with the nature of the component, less of the highly active noble metals, particularly platinum, being required than of the less active metals.

It may be desirable to incorporate the catalyst in another material resistant to the temperature and other conditions employed in the process. Such matrix materials include synthetic or natural substances as well as inorganic materials such as clay, silica and/or metal oxides. The latter may be either naturally occurring or in the form of gelatinous precipitates or gels including mixtures of silica and metal oxides. Naturally occurring clays which can be composited with the catalyst include those of the montmorillonite and kaolin families. These clays can be used in the raw state as originally mined or initially subjected to calcination, acid treatment or chemical modification.

The catalyst may be composited with a porous matrix material, such as alumina, silica-alumina, silica-magnesia, silica-zirconia, silica-beryllia or silica-titania or ternary compositions, such as silica-alumina-thoria, silica-alumina-zirconia, silica-alumina-magnesia, and silica-magnesia zirconia. The matrix may be in the form of a cogel with the zeolite. The relative proportions of zeolite component and inorganic oxide gel matrix may vary widely with the zeolite content ranging from between 1 to 99, more usually 5 to 80, percent by weight of the composite. The matrix may itself possess catalytic properties generally of an acidic nature.

Process Conditions

The feedstock is contacted with the zeolite in the presence or absence of added hydrogen at elevated temperature and pressure. Temperatures are normally from 150° C. to 500° C. (about 300° to 930° F.) preferably 250° C. to 350° C. (about 480° to 660° F.) although temperatures as low as 200° C. may be used especially if the feedstock is wholly or mostly comprised of pure paraffins. Because cracking reactions tend to increase with increasing temperatures, lower temperatures will normally be preferred in order to favor the isomerization over the cracking. Pressures range from atmospheric up to 25,000 kPa (3,600 psig) and although the higher pressures are preferred, practical considerations generally limit the pressure to a maximum of 15,000 kPa (2,160 psig), more usually in the range 4,000 to 10,000 kPa (565 to 1,435 psig). Space velocity is generally from 0.1 to 10 $hr^{-1}$ more usually 0.2 to 5 $hr^{-1}$. If additional hydrogen is present, the hydrogen:feedstock ratio is generally from 200 to 4,000 $n.l.l^{-1}$ (1,125 to 22,470 SCF/bbl), preferably 600 to 2,000 $n.l.l^{-1}$ (3,370 to 11,235 SCF/bbl).

If the feedstock is in the distillate range (165°–340° C., about 330°–650° F.) the isomerization should be carried out at a relatively low pressure, typically 1500 to 5600 kPa (about 200 to 800 psig) but if the feedstock is a lubricating oil stock, higher pressures will be appropriate, generally above 7000 kPa (about 1000 psig) and usually in the range 7000 to 22000 kPa (about 1000 to 3000 psig).

The selectivity of the process for isomerization has been found to increase at higher space velocities, pressures, relative hydrogen pressures and metal loadings on the catalyst and also with lower temperatures. The use of higher space velocities will permit higher temperatures as will the use of more highly noble metals as the hydrogenation component of the catalyst. As the boiling point of the feedstock components increases, the selectivity for isomerization as against cracking will decrease although compensation may be made for this by using zeolites with higher silica:alumina ratios which also permit the use of higher temperatures.

The process is preferably carried out in the presence of hydrogen, both to inhibit catalyst aging and to promote the isomerization reactions which are thought to proceed through an olefinically unsaturated intermediate.

The conversion may be conducted by contacting the feedstock with a fixed stationary bed of catalyst, a fixed fluidized bed or with a transport bed. A simple configuration is a trickle-bed operation in which the feed is allowed to trickle through a stationary fixed bed. With such a configuraton, it is desirable to initiate the reaction with fresh catalyst at a moderate temperature which is raised if the catalyst ages, in order to maintain catalytic activity. The catalyst may be regenerated by contact at elevated temperature with hydrogen gas, for example, or by burning in air or other oxygen-containing gas.

A preliminary hydrotreating step to remove nitrogen and sulfur and to saturate aromatics to naphthenes without substantial boiling range conversion will usually improve catalyst performance and permit lower temperatures, higher space velocities, lower pressures or combinations of these conditions to be employed.

During the isomerization process the $C_{10+}$ straight chain n-paraffins are converted to branched chain isoparaffins which not only have lower intrinsic pour points but also superior octane numbers and diesel indices. During the isomerization, the conversion of the $C_{10+}$ components to gasoline and lighter boiling range materials is minimized so that the product contains little or no $C_{10-}$ material beyond what may have been present in the original feedstock. Thus, there is substantially no conversion to material boiling below the distillate range i.e. below about 165° C. (330° F.)

The invention is illustrated in the following Examples in which all percentages and proportions are by weight unless the contrary is stated.

Examples 1 to 8 below illustrate the preparation of highly siliceous zeolite beta. Example 9 illustrates the preparation of highly siliceous zeolite ZSM-20. Example 10 illustrates the preparation of highly siliceous zeolite Y.

EXAMPLES 1-5

Samples of zeolite beta in the hydrogen form and having a silica:alumina ratio of 30:1 and a crystallinity of 100 percent were treated with excess hydrochloric acid of ranging normality at 25° C. or 95° C. under reflux for ranging periods as shown in Table 2 below. The silica:alumina ratios of the products were determined by ammonia desorption thermogravimetric analysis (TGA) and the crystallinities by X-ray peak area determination. The results are shown in Table 1 below.

TABLE 1

Dealuminization of Zeolite Beta

| Ex | Treatment | Framework $SiO_2/Al_2O_3$ | Crystallinity (%) |
|---|---|---|---|
| 1 | 0.1 N HCl, 25°, 1 hr. | 40 | 100 |
| 2 | 0.1 N HCl, 95°, 1 hr. | 40 | 100 |
| 3 | 1 N HCl, 95°, 1 hr. | 190 | 85 |
| 4 | 2 N HCl, 95°, 1 hr. | 280 | 75 |
| 5 | 2 N HCl, 95°, 2 hr. | 400 | — |

Comparison of Examples 1 and 2 shows that the dealumination proceeds readily both at ambient and mildly elevated temperatures, although the degree of dealuminization effected is quite small with acid of this concentration. Use of more concentrated acid, as in Examples 3 and 4, gives a far greater degree of dealuminization a slight loss of crystallinity occurs but the product remains essentially a crystalline zeolite. Prolonged treatment, as shown in Example 5 produces a further increase in silica:alumina ratio with a relatively smaller loss in crystallinity, indicating the greater stability of the zeolite to acid attack at higher silica:alumina ratios.

EXAMPLES 6-8

Samples of zeolite beta having silica:alumina ratios (bulk assay) of 21.3:1, 23:1 and 35:1 were calcined in flowing nitrogen, increasing the temperature from room temperature to 500° C. at 1°/minute, and then holding at 500° C. for 4 hours. At 500° C. the zeolites were air calcined by increasing the air concentration from 15 to 30, 50, 70 and, finally, to 100 percent at 30 minute intervals and holding in 100 percent air for an additional 5 hours.

About 5 grams each of the calcined zeolites were then treated as follows:

| 0.1 N HCl, | 95°, 1 hour |
|---|---|
| 1 M NH$_4$Cl, | 95°, 1 hour |
| 2.0 N HCl, | 95°, 1 hour |
| 1 M NH$_4$Cl, | 95°, 1 hour |

The results are summarized in Table 2 below.

TABLE 2

Dealuminization of Zeolite Beta

| Ex | Initial $SiO_2/Al_2O_3$ | Final $SiO_2/Al_2O_3$ |
|---|---|---|
| 6 | 21.3 | 280, 250* |
| 7 | 23 | 195 |
| 8 | 35 | 150 |

*Large sample (15 g.) used for this determination.

EXAMPLE 9

Ammonium exchanged TEA NaZSM-20 (silica:alumina ratio 10:1) was calcined in flowing nitrogen at 300° C. for 4 hours, followed by heating to a final temperature of 500° C. over an additional 4 hours. The HNaZSM-20 so produced was ammoniated and then ammonium exchanged with 0.5 M NH$_4$Cl under reflux at 100° C., washed free of chloride with water and dried at 120° C. The NH$_4$ZSM-20 was then calcined at 760° C. for 3 hours in a tightly packed and covered crucible to prevent ammonia and water from escaping readily. The ultrastable HZSM-20 (US) was ammoniated and ammonium exchanged with 1M NH$_4$Cl under reflux at 100° C. for 1 hour, washed with water and dried at 120° C. The dried NH$_4$ZSM-20 (US) was calcined at 815° C. for 3 hours in a tightly packed and covered crucible and after cooling the calcined product was slurried in water (2.5 g. zeolite per 200 ml water) and 1N HCl added slowly to obtain a 0.2N HCl concentration. The slurry was refluxed for 1 hour at 100° C. to form dealuminized HZSM-20 (USD) which was washed with water and dried at 120° C.

The product had a silica:alumina ratio of 226:1 by TGA/NH$_3$ desorption (20° C., min$^{-1}$, helium sweep), a crystallinity of 55 percent relative to an assumed value of 100 percent for the original NH$_4$ZSM-20 (crystallinity by X-ray peak determination) and an n-hexane cracking activity of 0.01 compared to 0.76 for the original NH$_4$ZSM-20 (100 mg sample at 400° C. for minutes at 100 torr in helium, sample calcined in air at 540° C. prior to use).

EXAMPLE 10

A sample of NaY zeolite having a silica:alumina ratio of 5.23:1 by bulk assay was converted to ultrastable zeolite Y by ammonium exchange and calcination in nitrogen as described above in Example 9, followed by ammoniation and ammonia exchange and deep bed calcination at 760° C. for 3 hours in a tightly packed and covered crucible. The ultrastable zeolite Y, HY(US), so formed was again ammoniated and ammonium exchanged, followed by deep bed calcination at 815° C. for 3 hours.

Samples of the ultrastable zeolite Y were then extracted with HCl at 90° C. for 4 hours, using different acid concentrations. The extracted samples were then analyzed for structural silica:alumina ratio by bulk assay and TGA/NH$_3$ desorption. The n-hexane cracking activity was also determined using the same conditions as in Example 9. The results are set out in Table 3 below.

TABLE 3

Dealuminization of Zeolite Y

| SAMPLE ALPHA DESCRIPTION | PREPARATION | SiO$_2$/Al$_2$O$_3$ BULK ASSAY | SiO$_2$/Al$_2$O$_3$ TGA—NH$_3$ | CRACKING ACTIVITY N—HEXANE | ALPHA |
|---|---|---|---|---|---|
| NaY | | 5.23 | — | — | — |
| NH$_4$Y(US) | 760° C., 3 hrs covered | — | 3.47 | 0.54 | — |
| NH$_4$Y(US2D)0.2 | 815° C., 3 hrs covered 0.2 NHCl 90° C. 4 hrs | 19.5 | 40.8–75.6[1] | 0.11 | — |
| NH$_4$Y(US2D)0.5 | 0.5 NHCl, 90° C. 4 hrs | 19.7 | 48.8 | 0.153 | 735 |
| NH$_4$Y(US2D)2.0 | 2.0 NHCl, 90° C. 4 hrs | 279 | 1027 | 0.00015[2] | 0.4 |
| NH$_4$Y(US2D)0.2 | 0.2 NHCl, 90° C. 4 hrs | 10 | 36–75.2[1] | 0.095 | — |

Notes:
[1] Initial value prior to calcination at 500° C., pH decreases during titration above 600° C. in TGA.
[2] Calculated from alpha and corrected to 750° F. at 30 kcal E$_a$.

EXAMPLES 11–15

Samples of five different zeolites were tested for isomerization activity using n-hexadecane as the feedstock. The zeolites were a low sodium NH$_4$-Y zeolite of silica:alumina ratio 5:1 (Example 11), a commercial ultrastable zeolite Y from Linde (Example 12), a dealuminized zeolite Y with a silica:alumina ratio of 75:1 (Example 13) and two samples of zeolite beta in the as-synthesized form with silica:alumina ratios of 30:1 and 80:1, respectively (Examples 14 and 15). Table 4 below presents the silica:alumina ratios of these zeolites, both by bulk assay and TGA/NH$_3$ desorption. Both the ultrastable Y and the acid extracted dealuminized Y zeolites contain considerable non-framework aluminum.

TABLE 4

Analysis of Zeolites

| Example | Zeolite | SiO$_2$/Al$_2$O$_3$ Bulk Assay | SiO$_2$/Al$_2$O$_3$ (Framework by TGA) |
|---|---|---|---|
| 11 | Y | 5 | 6 |
| 12 | USY | 5 | 25 |
| 13 | De-Al Y | 10 | 75 |
| 14 | Beta | 25 | 30 |
| 15 | Beta | 80 | 85 |

The as-synthesized zeolites were calcined in flowing nitrogen at 500° C. for 4 hours followed by air at the same temperature for 1 hour. The five zeolites were exchanged to the ammonium form with 1M NH$_4$Cl solution at 90° C. reflux for an hour. They were then calcined in flowing nitrogen at 500° C. for 4 hours and given an additional NH$_4$Cl exchange for an hour. Palladium was introduced into the zeolites by ion-exchange of the tetrammine complex at room temperature overnight. The palladium-exchanged material was thoroughly washed and then over dried at 130° C. The finished catalysts, which contain about 2% Pd by weight, were pelleted, crushed and sized to 30–40 mesh (Tyler—about 0.35 to 0.5 mm) before use.

The catalyst (1 cc) was mixed with 3 cc of 30–40 mesh (Tyler) washed quartz chips ("Vycor") and then loaded into the stainless steel reactor. The catalyst was reduced in flowing hydrogen at 370° C. for an hour at atmospheric pressure. Prior to the introduction of the liquid feed, the reactor was cooled to 250° C. and then pressurized with hydrogen to the desired pressure.

The liquid and gas products were collected at room temperture and atmospheric pressure and the combined gas and liquid recovery gave material balance of over 95%.

First, the three Y zeolites were tested at a temperature of 250° C.–315° C., 3,550 kPa, 2 LHSV, H$_2$/hexadecane—25:1. The results showing the proportions of the various products obtained are illustrated in FIG. 1 of the accompanying drawings. The Figure shows that the silica:alumina ratio of the catalyst has a significant effect on selectivity for isomerization (Iso): increasing the framework silica:alumina ratio reduces the number of acidic sites in the catalyst, resulting in reduced cracking and improved isomerization selectivity. In addition, the highly siliceous Pd/Y catalysts show very little aging while the low silica Pd/Y (SiO$_2$/Al$_2$O$_3$=5) catalyst deactivates very rapidly (more than 10° C. day$^{-1}$ at 40 percent conversion).

Figure 2:
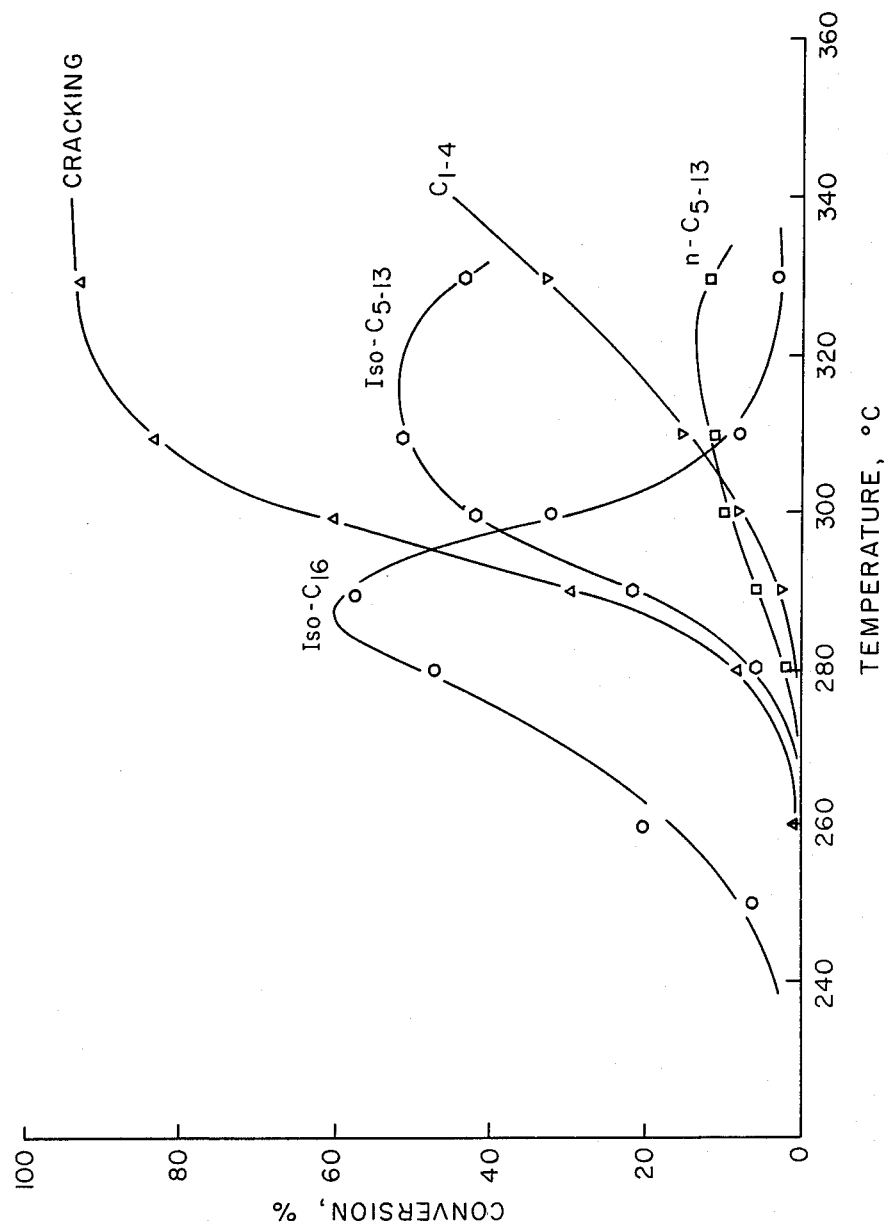

The results obtained with the Pd/De-Al Y catalyst at different temperatures (Example 13) are shown in FIG. 2. There is essentially no cracking up to about 40 percent conversion and the maximum isomerization yield is about 60 percent at 80 percent total conversion.

Figure 3:
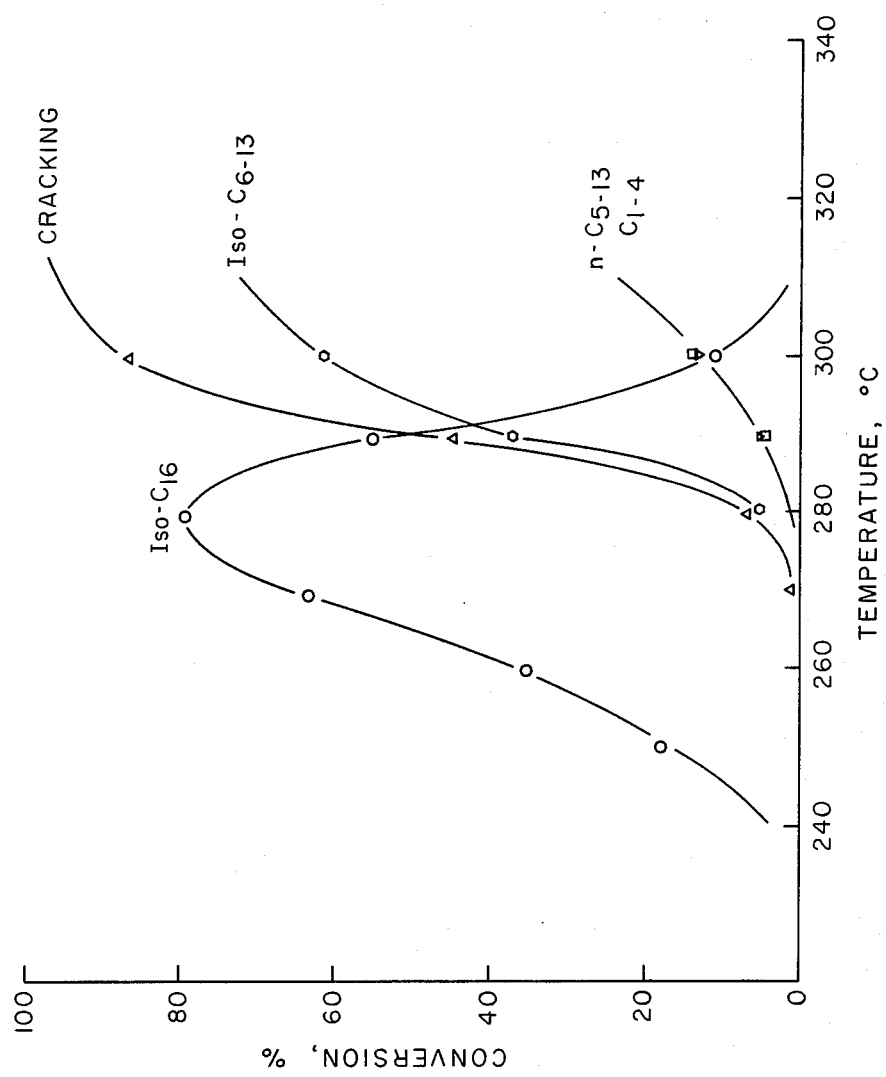
Figure 4:
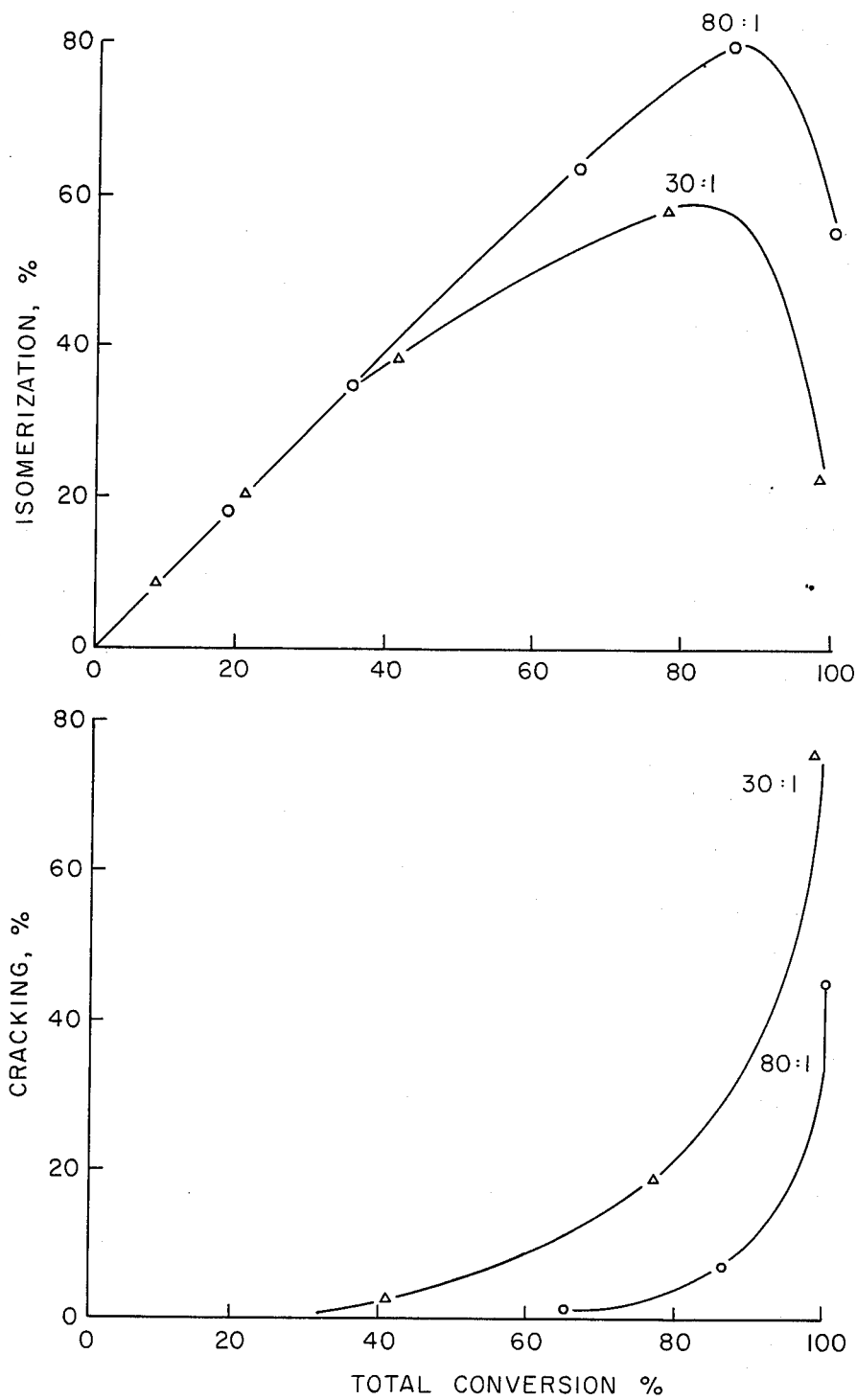

The results obtained with the two zeolite beta catalysts (Examples 14 and 15) are shown in FIGS. 3 and 4. FIG. 4 clearly shows the effect of the silica:alumina ratio. In addition, the beta based catalyst has better isomerization selectivity than the zeolite Y based catalyst at the same silica:alumina ratio (cf. FIG. 2).

A mixture of C$_{10}$–C$_{16}$ n-paraffins was also passed over the catalysts of Examples 13 and 15 in a further isomerization study. The composition of the feedstock is shown in Table 5 below:

TABLE 5

Mixed Paraffin Feedstock Composition

| Paraffin | Wt. Percent |
|---|---|
| n—C$_{10}$ | 16.6 |
| n—C$_{12}$ | 16.6 |
| n—C$_{13}$ | 16.6 |
| n—C$_{16}$ | 50.0 |

The feedstock was passed over the catalysts at 2 LHSV at 3,550 kPa at temperatures from 250° C. to 300° C. The results are given in Tables 6 and 7 below for the catalysts of Examples 13 and 15, respectively.

TABLE 6

Pd/De-Al Y Isomerization

| Paraffin | Conversion, Wt. Percent | | | |
|---|---|---|---|---|
| n—$C_{16}$ | 29.2 | 52.2 | 77 | 93.7 |
| n—$C_{13}$ | 12.8 | 19.7 | 32 | 52.8 |
| n—$C_{12}$ | 6.8 | 9.1 | 20 | 32.1 |
| n—$C_{10}$ | — | 7.7 | 14 | 15.2 |

TABLE 7

Pd/Beta (85:1)

| Paraffin | Conversion, Wt. Percent | | | |
|---|---|---|---|---|
| n—$C_{16}$ | 20 | 55.4 | 81.3 | 95.2 |
| n—$C_{13}$ | 7.5 | 17.9 | 31.7 | 55.2 |
| n—$C_{12}$ | 1.87 | 9.32 | 14.8 | 32.2 |
| n—$C_{10}$ | — | 5.4 | 8.6 | 15.1 |

The results in Tables 6 and 7 show that the longer chain paraffins are converted preferentially to the lighter ones.

Figure 6:
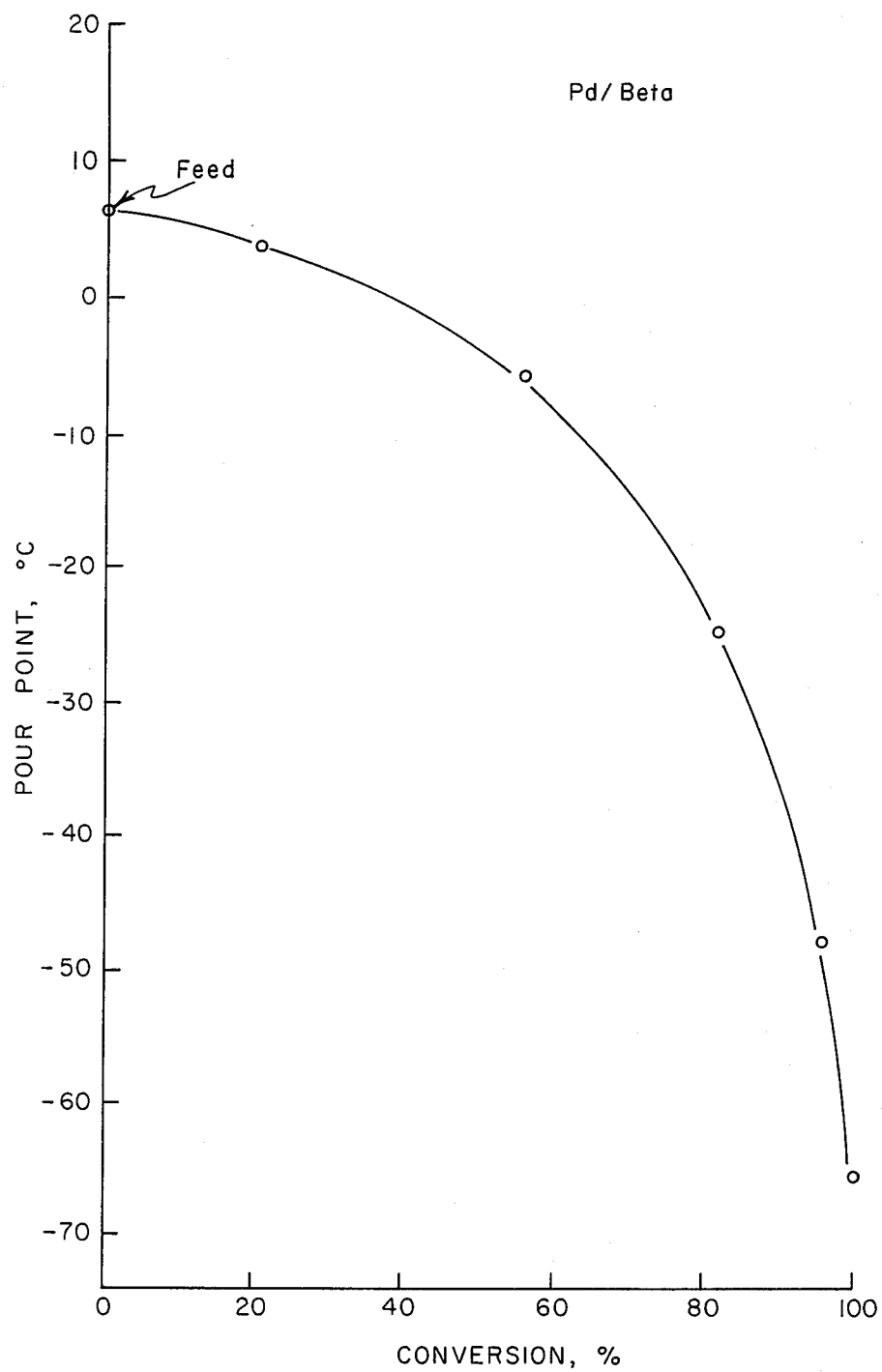

The product distribution for the catalysts of Examples 13 and 15 is shown in FIG. 5 as a function of n-$C_{16}$ conversion. The pour point of the $C_{10+}$ liquid product is shown in FIG. 6 as a function of $C_{16}$ conversion and it will be noted that a high yield of low pour point product can be obtained by the selective isomerization of long chain paraffins using the present isomerization process. In this way, the waxy feedstock is effectively dewaxed with a minimal degree of cracking.

Figure 7:
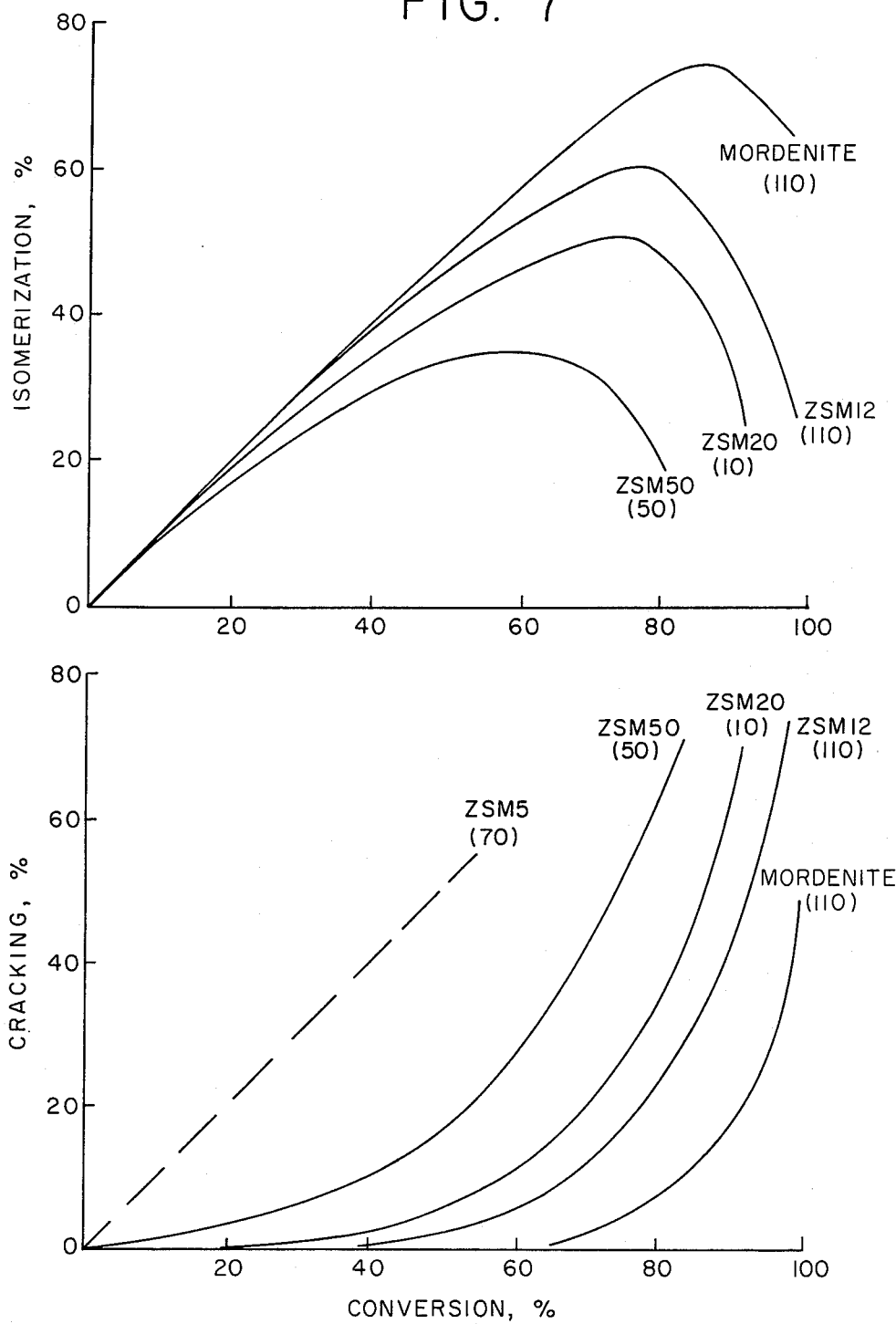

FIG. 7 summarizes the relative isomerization and cracking activities of the various zeolites at different total conversions and for different silica:alumina ratios in the zeolites (values of the ratio given parenthetically in the Figure).

We claim:

1. An isomerization process in which a hydrocarbon feedstock comprising $C_{10}+$ n-paraffins wherein the aromatic content of the feedstock is less than about 20 weight percent of the feedstock, is contacted under isomerization conditions with a catalyst comprising a large pore zeolite selected from the group consisting of ZSM-20 and zeolite Y having a silica/alumina ratio greater than 10:1 and a hydrocarbon absorption capacity of at least 6 percent by weight at 50° C. and a hydrogenation component to convert at least a portion of said n-paraffins to iso-paraffins.

2. An isomerization process in which a hydrocarbon feedstock comprising long chain n-paraffins having an initial boiling point of at least 150° C. is contacted, under isomerization conditions including a temperature of 150° C. to 500° C., with a catalyst comprising ZSM-20 having a framework silica/alumina ratio greater than 10:1 and a hydrogenation component to convert the n-paraffins to isoparaffins.

3. A process according to claim 2 in which the hydrocarbon feedstock has a boiling range of 150° C. to 560° C.

4. A process according to claim 3 in which the hydrocarbon feedstock has a boiling range of 340° C. to 540° C.

5. A process according to claim 2 in which the zeolite has a silica:alumina ratio of at least 50:1.

6. A process according to claim 5 in which the zeolite has a silica:alumina ratio of at least 100:1.

7. A process according to claim 2 in which the hydrogenation component is a metal of Group VIIIA of the Periodic Table.

8. A process according to claim 7 in which the hydrogenation component comprises platinum.

9. A process according to claim 7 in which the hydrogenation component comprises palladium.

10. A process according to claim 2 in which the feedstock is contacted with the catalyst in the presence of hydrogen.

11. A process according to claim 2 in which the feedstock is contacted with the catalyst at a temperature from 150° C. to 500° C., a pressure up to 25,000 kPa and a space velocity of 0.1 to 10.

12. A process for isomerizing long chain n-paraffins comprising contacting a hydrocarbon feedstock comprising $C_{10}+$ n-paraffins having an aromatic content of less than about 20 weight percent, under isomerization conditions, including a temperature of 150° to 500° C., with a catalyst comprising (i) an acidic component which is zeolite Y having a framework silica/alumina ratio greater than 25:1 and (ii) a hydrogenation component; and recovering product which includes the n-paraffins converted to isoparaffins.

13. A process according to claim 12 in which the hydrocarbon feedstock has a boiling range of 150° C. to 560° C.

14. A process according to claim 12 in which the zeolite has a silica:alumina ratio of at least 50:1.

15. A process according to claim 13 in which the zeolite has a silica:alumina ratio of at least 50:1.

16. A process according to claim 13 in which the zeolite has a silica:alumina ratio of at least 100:1.

17. A process according to claim 12 in which the hydrogenation component is a metal of Group VIIIA of the Periodic Table.

18. A process according to claim 17 in which the hydrogenation component comprises platinum.

19. A process according to claim 17 in which the hydrogenation component comprises palladium.

20. A process according to claim 12 in which the feedstock is contacted with the catalyst in the presence of hydrogen.

21. A process according to claim 12 in which the feedstock is contacted with the catalyst at a temperature from 250° C. to 500° C., a pressure up to 25,000 kPa and a space velocity of 0.1 to 10.

22. The process of claim 11, which further includes feeding hyddrogen during said contacting.

23. A process for catalytically isomerizing $C_{10}+$ n-paraffins comprising contacting a hydrocarbon feedstock comprising $C_{10}+$ n-paraffins wherein the aromatic content of the feedstock is less than about 20 weight percent of the feedstock and the initial boiling point of the feedstock is at least 150° C., under isomerization conditions, with a catalyst comprising (i) an acidic component which is a zeolite having a framework silica/alumina ration greater than 10:1 selected from the group consisting of ZSM-20, zeolite Y, ZSM-50, and ZSM-12, and (ii) a hydrogenation component; and recovering $C_{10}+$ n-paraffins, with $C_{10}$ minus material content substantially equal to that of the feed.

24. The process of claim 23, wherein said isomerization conditions include a temperature of about 150° C. to 500° C.

25. The process of claim 23, wherein the isomerization conditions include a temperature of about 250° C. to about 350° C.

26. A process according to claim 23 in which the hydrocarbon feedstock has a boiling range of 150° C. to 560° C.

27. A process according to claim 23 in which the zeolite has a silica:alumina ratio of at least 50:1.

28. A process according to claim 23 in which the zeolite has a silica:alumina ratio of at least 100:1.

29. A process according to claim 23 in which the hydrogenation component is a metal of Group VIIIA of the Periodic Table.

30. A process according to claim 29 in which the hydrogenation component comprises platinum.

31. A process according to claim 29 in which the hydrogenation component comprises palladium.

32. A process according to claim 23 in which the feedstock is contacted with the catalyst in the presence of hydrogen.

33. A process according to claim 27 in which the feedstock is contacted with the catalyst at a pressure up to 25,000 kPa and a space velocity of 0.1 to 10.

* * * * *